(12) United States Patent
Tagliaferri (10) Patent No.: US 10,576,121 B2
(45) Date of Patent: Mar. 3, 2020

(54) COMPOSITION AND METHOD FOR THE TREATMENT OF MENOPAUSE

(71) Applicant: Mary Tagliaferri, San Anselmo, CA (US)

(72) Inventor: Mary Tagliaferri, San Anselmo, CA (US)

(73) Assignee: Mary Tagliaferri, San Anselmo, CA (US)

( * ) Notice: Subject to any disclaimer, the term of this patent is extended or adjusted under 35 U.S.C. 154(b) by 247 days.

(21) Appl. No.: 15/514,476

(22) PCT Filed: Sep. 25, 2015

(86) PCT No.: PCT/US2015/052417
§ 371 (c)(1),
(2) Date: Mar. 24, 2017

(87) PCT Pub. No.: WO2016/049561
PCT Pub. Date: Mar. 31, 2016

(65) Prior Publication Data
US 2017/0281707 A1    Oct. 5, 2017

Related U.S. Application Data

(60) Provisional application No. 62/056,370, filed on Sep. 26, 2014.

(51) Int. Cl.
| | |
|---|---|
| *A61K 36/8945* | (2006.01) |
| *A61K 36/804* | (2006.01) |
| *A61K 36/884* | (2006.01) |
| *A61K 36/8964* | (2006.01) |
| *A61K 36/076* | (2006.01) |
| *A61K 36/284* | (2006.01) |
| *A61K 36/40* | (2006.01) |
| *A61K 9/14* | (2006.01) |
| *A61K 9/16* | (2006.01) |
| *A61K 9/19* | (2006.01) |

(52) U.S. Cl.
CPC .......... *A61K 36/8945* (2013.01); *A61K 9/148* (2013.01); *A61K 9/16* (2013.01); *A61K 9/19* (2013.01); *A61K 36/076* (2013.01); *A61K 36/284* (2013.01); *A61K 36/40* (2013.01); *A61K 36/804* (2013.01); *A61K 36/884* (2013.01); *A61K 36/8964* (2013.01)

(58) Field of Classification Search
None
See application file for complete search history.

(56) References Cited

U.S. PATENT DOCUMENTS

| | | |
|---|---|---|
| 7,482,029 B2 | 1/2009 | Cohen |
| 8,110,228 B2 | 2/2012 | Cohen |
| 8,329,750 B2 | 12/2012 | Berner et al. |

FOREIGN PATENT DOCUMENTS

| | | |
|---|---|---|
| CN | 104524337 A | 4/2015 |
| WO | WO 2016/049561 A1 | 3/2016 |

OTHER PUBLICATIONS

Jacobs, et al., Integrative Cancer Therapies, 2:289. (Year: 2003).*
Giovanni Maciocia, "The Treatment of Menopausal Problems," (http://maciociaonline.blogspot.com/2012/09/the-treatment-of-menopausal-problems.html). (Year: 2012).*
Chen et al., "Use of Chinese herbal medicine among menopausal women in Taiwan", Int. J. Gynecol. Obstet., vol. 109, No. 1, pp. 63-66 (2010).
Chen et al., "Prescription patterns of Chinese herbal products for menopausal syndrome: analysis of a nationwide prescription database", J. Ethnopharmacol., vol. 137, No. 3, pp. 1261-1266 (2011).
Dharmananda, "The treatment of menopausal syndrome with Chinese herbs", Online article retrieved from the internet from: http://www.itmonline.org/arts/menopaus.htm, 10 pages (Mar. 1999).
Gold et al., "Longitudinal analysis of the association between vasomotor symptoms and race/ethnicity across the menopausal transition: study of women's health across the nation", Am. J. Public Health., vol. 96, No. 7, pp. 1226-1235 (2006).
Grady, "Clinical practice. Management of menopausal symptoms", N. Engl. J. Med., vol. 355, No. 22, pp. 2338-2347 (2006).
International Search Report from PCT Patent Application No. PCT/US2015/052417 dated Nov. 13, 2015, application now published as International Publication No. WO2016/049561 dated Mar. 31, 2016.
Nelson et al., "Management of menopause-related symptoms", Evidence Report/Technology Assessment, No. 120, AHRQ Publication No. 05-E016-2, 916 pages (2005).
Rossouw et al., "Risks and benefits of estrogen plus progestin in healthy postmenopausal women: principal results From the Women's Health Initiative randomized controlled trial", JAMA, vol. 288, No. 3, pp. 321-333 (2002).
Stearns et al., "Hot flushes", Lancet., vol. 360, No. 9348, pp. 1851-1861 (2002).

\* cited by examiner

*Primary Examiner* — Michael Barker
(74) *Attorney, Agent, or Firm* — McDermott Will & Emery LLP; Judy M. Mohr; Wen Li

(57) ABSTRACT

Provided herein are compositions comprising an herbal extract of a mixture of Radix Rehmanniae, Fructus *Corni Officinalis*, Radix Dioscoreae Oppositae, Sclerotium Poriae Cocos, Cortex Moutan Radicis, Rhizoma *Alismatis Orientalis*, Anemarrhena Rhizome, *Glycyrrhiza uralensis*, Radix Astragali, and Atractylodis Macrocephalae Rhizoma. The invention also relates to a method of treating hot flashes associated with peri-menopause, menopause, or post-menopause, a method of reducing total cholesterol and/or lowering low density lipoprotein (LDL) levels and a method of reducing weight and/or body mass index (BM I) using the above mentioned herbal extract.

7 Claims, 3 Drawing Sheets

COMPOSITION AND METHOD FOR THE TREATMENT OF MENOPAUSE

CROSS-REFERENCE TO RELATED APPLICATIONS

This application is a U.S. National Stage of International Patent Application No. PCT/US2015/052417, filed Sep. 25, 2015, which claims the benefit of priority to U.S. Provisional Application No. 62/056,370, filed Sep. 26, 2014, each of which is incorporated herein by reference in its entirety.

TECHNICAL FIELD

The disclosure relates generally to a composition, and method for treating menopause, or the symptoms thereof, and related features thereof.

BACKGROUND

Vasomotor symptoms are reported by 60-80% of menopausal women (Gold et al., *Am J Public Health,* 2006, 96:1226-35) and approximately one-third of this population reports symptoms severe enough to seek treatment (Stearns et al., *Lancet,* 2002, 360:1851-1861). Vasomotor symptoms include hot flashes, hot flushes, and night sweats. Hot flashes are manifested as in increase in skin temperature and are often accompanied by a sudden onset of sweating on the face, neck and/or chest. Hot flashes and other vasomotor symptoms are commonly, but not exclusively, associated with females in a perimenopausal, menopausal or postmenopausal state.

The currently preferred treatment for menopausal symptoms, including vasomotor symptoms, is hormone replacement therapy using either estrogen or an estrogen/progesterone combination. While estrogens are an effective treatment for vasomotor symptoms (Nelson et al., AHRQ Publication No. 05-E016-2, 2005), concerns have been raised about the increased risk of uterine cancer, breast cancer and cardiovascular events associated with use of estrogen-based postmenopausal hormone therapy. Estrogen therapy is also contraindicated in patients previously diagnosed with breast cancer as estrogen and progesterone may be associated with an increased risk of cancer recurrence and are known to specifically promote growth of breast cancer cell with estrogen receptors. The use of selective serotonin reuptake inhibitors have shown modest efficacy in the treatment of hot flashes but have side effects that limit their use (Grady, *N Engl J Med,* 2006, 355:2338-47).

There are also numerous non-hormonal remedies commonly used by women suffering hot flashes including, for example, isoflavone, black cohosh, vitamin E, and the antidepressants fluoxetine, paroxetine, and venlafaxine. However, efficacy of these remedies is less than that of the hormone replacement therapies. A clinical trial with the plant-derived ERβ-selective extract, MF101 found a significant reduction of hot flashes in postmenopausal women (see U.S. Pat. No. 7,482,029).

Thus, there is a need for therapeutic compositions and methods for the treatment of the symptoms of perimenopause, menopause and/or postmenopause including hot flashes. There is a particular need for therapeutic compositions for the treatment or amelioration of menopausal symptoms that does not promote or increase the risk of cancers including breast cancer and uterine cancer.

BRIEF SUMMARY

The following aspects and embodiments described and illustrated below are meant to be exemplary and illustrative, and are no way intended to be limiting in scope.

In a first aspect, provided is a composition comprising or consisting essentially of herbal extracts of Radix Rehmanniae, Fructus *Corni Officinalis*, Radix Dioscoreae Oppositae, Sclerotium Poriae Cocos, Cortex Moutan Radicis, Rhizoma *Alismatis Orientalis*, Anemarrhena Rhizome, *Glycyrrhiza uralensis*, Radix Astragali, and Atractylodis Macrocephalae Rhizoma. In one embodiment, the herbal extracts are present as about 12% Radix Rehmanniae, about 12% Fructus *Corni Officinalis*, about 12% Radix Dioscoreae Oppositae, about 10% Sclerotium Poriae Cocos, about 10% Cortex Moutan Radicis, about 10% Rhizoma *Alismatis Orientalis*, about 10% Anemarrhena Rhizome, about 10% *Glycyrrhiza uralensis*, about 6% Radix Astragali, and about 8% Atractylodis Macrocephalae Rhizoma. In some embodiments, at least some of the herbal extracts are aqueous extracts. In some embodiments, at least some of the herbal extracts are formulated in one or more oils. In some embodiments, the oil is one or more vegetable oils. In some specific embodiments, the oil is canola oil, olive oil, soybean oil, sunflower seed oil, peanut oil, palm oil, corn oil, sesame oil, and/or coconut oil. In a further embodiment, the composition is formulated as a spray-dried powder or a freeze-dried powder. In other embodiments, the composition is formulated as a capsule or tablet.

In another aspect, compositions are provided for use in treating, preventing, or ameliorating one or more symptoms of peri-menopause, menopause, and or post-menopause. In an embodiment, the composition is for use in treating, preventing, or ameliorating hot flashes. In another aspect, compositions are provided for use in reducing total cholesterol and/or lowering or reducing low density lipoprotein levels. In another aspect, compositions are provided for use in reducing weight and/or lowering a subject's body mass index. In some embodiments, a dose of about 500-4000 mg of the combined herbal extracts is administered daily, weekly, or monthly. In some embodiments, about 0.1-10 mg/kg of the composition is administered daily, weekly, or monthly. In some embodiments, the composition is administered for a period of about 4-52 weeks or more. In one embodiment, the composition is administered about 30-60 minutes after a meal.

Additional embodiments of the present compositions, methods, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention.

Additional aspects and advantages of the present invention are set forth in the following description and claims, particularly when considered in conjunction with the accompanying examples and drawings.

BRIEF DESCRIPTION OF DRAWINGS

FIG. 1A shows the effect of the composition at 10, 25, 50, or 100 μg/ml, a control, and $E_2$ on ERα expressing cells as measured by luciferase activity in relative light units (RLU). FIG. 1B compares the effect of the composition at 10, 25, 50, or 100 μg/ml, a control, and $E_2$ on ERβ expressing cells as measured by luciferase activity in relative light units (RLU).

DETAILED DESCRIPTION

Various aspects of the compositions and related methods will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

The practice of the present disclosure will employ, unless otherwise indicated, conventional methods of chemistry, biochemistry, and pharmacology, within the skill of the art. Such techniques are explained fully in the literature. See, e.g.; A. L. Lehninger, *Biochemistry* (Worth Publishers, Inc., current addition); Morrison and Boyd, *Organic Chemistry* (Allyn and Bacon, Inc., current addition); J. March, *Advanced Organic Chemistry* (McGraw Hill, current addition); *Remington: The Science and Practice of Pharmacy*, A. Gennaro, Ed., 20$^{th}$ Ed.; *Goodman & Gilman The Pharmacological Basis of Therapeutics*, J. Griffith Hardman, L. L. Limbird, A. Gilman, 10$^{th}$ Ed.

Where a range of values is provided, it is intended that each intervening value between the upper and lower limit of that range and any other stated or intervening value in that stated range is encompassed within the disclosure. For example, if a range of 1 μg to 5 μg is stated, it is intended that 2 μg, 3 μg, 4 μg, and 5 μg are also explicitly disclosed, as well as the range of values greater than or equal to 1 μg and the range of values less than or equal to 5 μg.

I. DEFINITIONS

As used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

In describing and claiming the present invention, the following terminology will be used in accordance with the definitions described below.

An "herbal extract" as used herein refers generally to substance that is obtained by extracting a portion of an herb, usually by use of a solvent.

As used herein, "menopause" or "menopausal" includes perimenopause, menopause, and post-menopause.

"Optional" or "optionally" means that the subsequently described circumstance may or may not occur, so that the description includes instances where the circumstance occurs and instances where it does not.

"Substantially" or "essentially" means nearly totally or completely, for instance, 90% or greater of some given quantity.

II. OVERVIEW

The present disclosure is directed, at least in part, to the discovery of composition comprising extracts from ten botanical agents that acts as a selective estrogen receptor beta agonist and is useful for the treatment of the symptoms of peri-menopause, menopause, and post-menopause. The present disclosure is further directed to the discovery of the composition for use in lowering total cholesterol and/or low density lipoproteins. The present disclosure is also directed to the discovery of the composition for use in lowering a subject's weight and/or body mass index (BMI).

III. COMPOSITION

Estrogen signaling pathways are mediated by the estrogen receptor α (ERα) and estrogen receptor β (ERβ) estrogen receptors. Studies have suggested that drugs selectively targeted to the ERα or the ERβ estrogen receptor may produce more selective clinical effects. However, studies have shown that the proliferative effects on endometrial and breast cells associated with hormone replacement therapy are mediated by ERα. Thus, the adverse effects associated with hormone replacement therapy may be due to activation of ERα. The present compositions selectively activate the estrogen response element (ERE) with ERβ.

The present compositions include a mixture of herbal extracts of Radix Rehmanniae, Fructus *Corni Officinalis*, Radix Dioscoreae Oppositae, Sclerotium Poriae Cocos, Cortex Moutan Radicis, Rhizoma *Alismatis Orientalis*, Anemarrhena Rhizome, *Glycyrrhiza uralensis*, Radix Astragali, and Atractylodis Macrocephalae Rhizoma. It will be appreciated that, in general, the composition includes herbal mixtures, extracts of herbal mixtures and mixtures of herbal extracts. In some embodiments, the composition comprises, consists essentially of, or consists of a mixture of the herbs or a mixture of herbal extracts in accord with Table 1:

TABLE 1

Exemplary Formulation

| Herbal Ingredient | Percent by weight | Weight in mg |
|---|---|---|
| Radix Rehmanniae | 5-20% | 30-600 |
| Fructus Corni Officinalis | 5-20% | 30-600 |
| Radix Dioscoreae Oppositae | 5-20% | 30-600 |
| Sclerotium Poriae Cocos | 5-15% | 25-500 |
| Cortex Moutan Radicis | 5-15% | 25-500 |
| Rhizoma Alismatis Orientalis | 5-15% | 25-500 |
| Anemarrhena Rhizome | 5-15% | 25-500 |
| Glycyrrhiza uralensis | 5-15% | 25-500 |
| Radix Astragali | 2-10% | 15-300 |
| Atractylodis Macrocephalae Rhizoma | 5-15 | 20-400 |

It will be appreciated that the percent by weight as described in Table 1 may refer to the percent by weight of the total composition weight or the percent by weight of the herbal ingredients. It will be appreciated that any or all of the herbs may be used in the composition including, but not limited to, the flower, fruit, leaves, stem, bark and/or roots as appropriate.

In embodiments, the formulation comprises about 30-600 mg, about 30-550 mg, about 30-500 mg, about 30-450 mg, about 30-400 mg, about 30-350 mg, about 30-300 mg, about 30-250 mg, about 30-200 mg, about 30-150 mg, about 30-120 mg, about 30-100, about 30-60, about 30-50, about 50-600 mg, about 50-550 mg, about 50-500 mg, about 50-450 mg, about 50-400 mg, about 50-350, about 50-300, about 50-250, about 50-200, about 50-150, about 50-120, about 50-100, about 50-60, about 60-600 mg, about 60-550 mg, about 60-500 mg, about 60-450 mg, about 60-400 mg, about 60-350, about 60-300, about 60-250, about 60-200, about 60-150, about 60-120, about 60-100, about 100-600 mg, about 100-550 mg, about 100-500 mg, about 100-450 mg, about 100-400 mg, about 100-350, about 100-300, about 100-250, about 100-200, about 100-150, about 100-120, about 120-600 mg, about 120-550 mg, about 120-500 mg, about 120-450 mg, about 120-400 mg, about 120-350, about 120-300, about 120-250, about 120-200, about 120-150, about 150-600 mg, about 150-550 mg, about 150-500 mg, about 150-450 mg, about 150-400 mg, about 150-350, about 150-300, about 150-250, about 150-200, about 200-600 mg, about 200-550 mg, about 200-500 mg, about 200-450 mg, about 200-400 mg, about 200-350, about 200-300, about 200-250, about 250-600 mg, about 250-550 mg, about 250-500 mg, about 250-450 mg, about 250-400 mg, about 250-350, about 250-300, about 300-600 mg, about 300-550 mg, about 300-500 mg, about 300-450 mg, about 300-400 mg, about 300-350, about 350-600 mg, about 350-550 mg, about 350-500 mg, about 350-450 mg, about 350-400 mg, about 400-600 mg, about 400-550 mg, about 400-500 mg, about 400-450 mg, about 450-600 mg, about 450-550 mg, about 450-500 mg, about 500-600 mg, about 500-550 mg, or about 550-600 mg of one or more of Radix Rehmanniae, Fructus *Corni Officinalis*, and/or Radix Dioscoreae Oppositae. In specific embodiments, the formulation comprises about 30 mg, about 40 mg, about 50 mg, about 60 mg, about 100 mg, about 120 mg, about 150 mg, about 180 mg, about 200 mg, about 240 mg, about 250 mg, about 300 mg, about 350 mg, about 360 mg, about 400 mg, about 420 mg, about 450 mg, about 480 mg, about 500 mg, about 540 mg, about 550 mg, or about 600 mg of one or more of Radix Rehmanniae, Fructus *Corni Officinalis*, and/or Radix Dioscoreae Oppositae. It will be appreciated that the amounts above may refer to the amount per capsule or the amount per daily, weekly or monthly dose.

In other embodiments, the formulation comprises about 25-500 mg, about 25-450 mg, about 25-400 mg, about 25-350, about 25-300, about 25-250, about 25-200, about 25-150, about 25-100, about 25-50, about 50-500 mg, about 50-450 mg, about 50-400 mg, about 50-350, about 50-300, about 50-250, about 50-200, about 50-150, about 50-100, about 75-500 mg, about 75-550 mg, about 75-500 mg, about 75-450 mg, about 75-400 mg, about 75-350, about 75-300, about 75-250, about 75-200, about 75-150, about 75-100, about 100-500 mg, about 100-450 mg, about 100-400 mg, about 100-350, about 100-300, about 100-250, about 100-200, about 100-150, about 150-500 mg, about 150-450 mg, about 150-400 mg, about 150-350, about 150-300, about 150-250, about 150-200, about 200-500 mg, about 200-450 mg, about 200-400 mg, about 200-350, about 200-300, about 200-250, about 250-500 mg, about 250-450 mg, about 250-400 mg, about 250-350, about 250-300, about 300-500 mg, about 300-450 mg, about 300-400 mg, about 300-350, about 350-500 mg, about 350-450 mg, about 350-400 mg, or about 450-500 mg of one or more of Sclerotium Poriae Cocos, Cortex Moutan Radicis, Rhizoma *Alismatis Orientalis*, and/or Anemarrhena Rhizome. In specific embodiments, the formulation comprises about 25 mg, about 50 mg, about 75 mg, about 100 mg, about 150 mg, about 200 mg, about 250 mg, about 300 mg, about 350 mg, about 400 mg, about 450 mg, or about 500 mg of one or more of Sclerotium Poriae Cocos, Cortex Moutan Radicis, Rhizoma *Alismatis Orientalis*, and/or Anemarrhena Rhizome. It will be appreciated that the amounts above may refer to the amount per capsule or the amount per daily, weekly or monthly dose.

In other embodiments, the formulation comprises about 15-300 mg, about 15-270 mg, about 15-250 mg, about 15-240 mg, about 15-210 mg, about 15-200 mg, about 15-180 mg, about 15-150 mg, about 15-120 mg, about 15-100 mg, about 15-90 mg, about 15-75 mg, about 15-60 mg, about 15-50 mg, about 15-45 mg, about 15-30 mg, about 15-25 mg, about 15-20 mg, about 25-300 mg, about 25-270 mg, about 25-250 mg, about 25-240 mg, about 25-210 mg, about 25-200 mg, about 25-180 mg, about 25-150 mg, about 25-120 mg, about 25-90 mg, about 25-100 mg, about 25-75 mg, about 25-60 mg, about 25-50 mg, about 30-300 mg, about 30-270 mg about 30-250 mg, about 30-240 mg, about 30-210 mg, about 30-200 mg, about 30-180 mg, about 30-150 mg, about 30-120 mg, about 30-100 mg, about 30-90 mg, about 30-75 mg, about 30-60 mg, about 30-50 mg, about 30-45 mg, about 45-300 mg, about 45-270 mg about 45-250 mg, about 45-240 mg, about 45-210 mg, about 45-200 mg, about 45-180 mg, about 45-150 mg, about 45-120 mg, about 45-100 mg, about 45-90 mg, about 45-75 mg, about 45-60 mg, about 45-50 mg, about 50-300 mg, about 50-270 mg about 50-250 mg, about 50-240 mg, about 50-210 mg, about 50-200 mg, about 50-180 mg, about 50-150 mg, about 50-120 mg, about 50-100 mg, about 50-90 mg, about 50-75 mg, about 50-60 mg, about 60-300 mg, about 60-270 mg about 60-250 mg, about 60-240 mg, about 60-210 mg, about 60-200 mg, about 60-180 mg, about 60-150 mg, about 60-120 mg, about 60-100 mg, about 60-90 mg, about 60-75 mg, about 75-300 mg, about 75-270 mg about 75-250 mg, about 75-240 mg, about 75-210 mg, about 75-200 mg, about 75-180 mg, about 75-150 mg, about 75-120 mg, about 75-100 mg, about 75-90 mg, about 90-300 mg, about 90-270 mg, about 90-250 mg, about 90-240 mg, about 90-210 mg, about 90-200 mg, about 90-180 mg, about 90-150 mg, about 90-120 mg, about 90-100 mg, about 100-300 mg, about 100-250 mg, about 100-200 mg, about 100-150 mg, about 120-300 mg, about 120-270 mg, about 120-250 mg, about 120-240 mg, about 120-210 mg, about 120-200 mg, about 120-180 mg, about 120-150 mg, about 150-300 mg, about 150-250 mg, about 150-200 mg, about 200-300 mg, about 200-250 mg, about 210-300 mg, about 210-270 mg, about 210-250 mg, about 120-240 mg, or about 250-300 mg, of Radix Astragali. In specific embodiments, the formulation comprises about 15 mg, about 20 mg, about 25 mg, about 30 mg, about 45 mg, about 50 mg, about 60 mg, about 75 mg, about 90 mg, about 100 mg, about 120 mg, about 150 mg, about 180 mg, about 200 mg, about 210 mg, about 240 mg, about 250 mg, or about 300 mg of Radix Astragali. It will be appreciated that the amounts above may refer to the amount per capsule or the amount per daily, weekly or monthly dose.

In embodiments, the formulation comprises about 20-400 mg, about 20-360 mg, about 20-350 mg, about 20-320 mg, about 20-300 mg, about 20-280 mg, about 20-250 mg, about 20-240 mg, about 20-200 mg, about 20-160 mg, about 20-150 mg, about 20-120 mg, about 20-100 mg, about 20-80 mg, about 20-75 mg, about 20-50 mg, or about 20-40 mg, about 40-400 mg, about 40-360 mg, about 40-350 mg, about 40-320 mg, about 40-300 mg, about 40-280 mg, about 40-250 mg, about 40-240 mg, about 40-200 mg, about 40-160 mg, about 40-150 mg, about 40-120 mg, about 40-100 mg, about 40-80 mg, about 40-75 mg, about 40-50 mg, about 50-400 mg, about 50-350 mg, about 50-300 mg, about 50-250 mg, about 50-200 mg, about 50-150 mg, about 50-100 mg, about 50-75 mg, about 80-400 mg, about 80-360 mg, about 80-350 mg, about 80-320 mg, about 80-300 mg, about 80-280 mg, about 80-250 mg, about 80-240 mg, about 80-200 mg, about 80-160 mg, about 80-150 mg, about 80-120 mg, about 80-100 mg, about 75-400 mg, about 75-350 mg, about 75-300 mg, about 75-250 mg, about 75-200 mg, about 75-150 mg, about 75-100 mg, about 100-400 mg, about 100-350 mg, about 100-300 mg, about 100-250 mg, about 100-200 mg, about 100-150 mg, about 120-400 mg, about 120-360 mg, about 120-350 mg, about 120-320 mg, about 120-300 mg, about 120-280 mg, about 120-250 mg, about 120-240 mg, about 120-200 mg, about 120-160 mg, about 120-150 mg, about 150-400 mg, about 150-350 mg, about 150-300 mg, about 150-250 mg, about 150-200 mg, about 160-400 mg, about 160-360 mg, about 160-350 mg, about 160-320 mg, about 160-300 mg, about 160-280 mg, about 160-250 mg, about 160-240 mg, about 160-200 mg, about 200-400 mg, about 200-350 mg, about 200-300 mg, about 200-250 mg, about 240-400 mg, about 240-360 mg, about 240-350 mg, about 240-320 mg, about 240-300 mg, about 240-280 mg, about 240-250 mg, about 250-400 mg, about 250-350 mg, about 250-300 mg, about 280-400 mg, about 280-360 mg, about 280-350 mg, about 280-320 mg, about 280-300 mg, about 300-400 mg, about 300-350 mg, about 320-400 mg, about 320-360 mg, about 320-350 mg, about 350-400 mg, or about 360-400 mg of Atractylodis Macrocephalae Rhizoma. In specific embodiments, the formulation comprises about 20 mg, about 40 mg, about 50 mg, about 60 mg, about 75 mg, about 80 mg, about 100 mg, about 120 mg, about 140 mg, about 150 mg, about 160 mg, about 200 mg, about 240 mg, about 250 mg, about 280 mg, about 300 mg, about 320 mg, about 350 mg, about 360 mg, or about 400 mg of Atractylodis Macrocephalae Rhizoma. It will be appreciated that the amounts above may refer to the amount per capsule or the amount per daily, weekly or monthly dose.

It will be appreciated that the formulation may include any of the ranges or specific amounts for each of the herbal ingredients as described above in combination.

Radix Rehmanniae, also known as Shu Di Huang, is a perennial, flowering herb. It has traditionally been used to treat fever, anemia, dizziness, palpitations, and uterine bleeding, among others. Typically, the root is used for treatment. Fructus *Corni Officinalis*, also known as Shan Zhu Yu, is a species of dogwood. It has traditionally been used to treat impotence, chronic lower back pain, incontinence, and excessive menstrual bleeding, among other conditions. Typically, the fruit is used for treatment. Radix Dioscoreae Oppositae, also known as Shan Yao, is used in traditional medicine to treat lack of appetite and energy, lower blood sugar and blood pressure, among other conditions. Typically, the tubers are used for treatment. Sclerotium Poriae Cocos, also known as Fu Ling, is a fungus traditionally used as a diuretic, and antibacterial, to lower blood sugar, and to treat gastrointestinal discomfort. Cortex Moutan Radicis, also known as, Mu Dan Pi, is a tree peony. It has been traditionally used to treat arthritis, typhus, nosebleed, fever, etc. Typically, the bark and/or root is used for treatment. Rhizoma *Alismatis Orientalis*, also known as Ze Xie, has traditionally been used as an anti-pyretic, an antibacterial, to treat hypotension and hypoglycemia, and as a diuretic, among others. Typically the tubers are used for treatment. Anemarrhena Rhizome, also known as Zhi Mu, has traditionally been used for high fever, congestion, dry throat, coughing, and pneumonia, among others. Typically, the root or rhizome is used for treatment. *Glycyrrhiza uralensis*, also known as Gan Cao, traditionally used to relieve stress and increase circulation. The root is typically used for treatment. Radix Astragali, also known as Huang Qi, has traditionally been used to treat colds, upper respiratory infections, allergies, diabetes, and high blood pressure, among others. Typically, the root is used for treatment. Atractylodis Macrocephalae Rhizoma, also known as Bai Zhu, is traditionally used for spleen disorders and to prevent miscarriage. Typically, the root or tuber is used for treatment.

The composition may include one or more excipients or additives including, but not limited to, fillers or binders, surfactants, wetting agents, and diluents. The compositions may further include one or more flavoring agents or sweeteners. Suitable diluents include water, e.g. deionized water, water for injection (WFI), filtered water, and purified water. Other suitable diluents include fruit juices, teas, and milk. Suitable flavorings include fruit flavorings, mint, including peppermint and spearmint, and cinnamon. Other suitable additives including food colorings and ethanol. In some embodiments, the composition comprises a dehydrated extract combined with one or more diluents, flavoring agents or other additives. In other embodiments, the composition comprises a reduced extract in combination with one or more diluents, flavoring agents or other additives.

The composition formulations may include suitable fillers, extenders, binders, wetting agents, surfactants, or other excipients as known in the art. In embodiments, the solid formulation may include tablets, pills, powders, granules, and capsules. Where the composition formulations are a powder, the powder may be formed by any suitable method including, but not limited to, spray drying or freeze drying. In some embodiments, the tablets, pills, or capsules may be coated. The coating may be functional (e.g. modifying release of the composition ingredients) or non-functional. In an embodiment, the coating provides sustained release of the herbal formulation. In another embodiment, the coating provides protection from irritant properties of one of more of the composition ingredients. Liquid formulations for oral administration may include suspensions, solutions, emulsions, and syrups. In one embodiment, the formulation may be added to an oil including, but not limited to olive oil, vegetable oil, and; or wheat germ oil. Parenteral formulations include sterilized aqueous solutions, water-insoluble solutions, suspensions, emulsions, and suppositories. In other embodiments, the compositions are formulated as a liquid, oral liposomal formulation, or as nanoparticles. In embodiments where the formulation or composition is administered by an oral route, the formulation may be administered with or after a meal to prevent irritation of the stomach. In one non limiting embodiment, the formulation or composition is administered 10 minutes to 1 hour after a meal. In particular, but not limiting embodiments, the formulation or composition is administered 10 minutes, 15 minutes, 20 minutes, 30 minutes, 45 minutes, or 60 minutes after a meal.

The compositions or formulations may be administered at a dose suitable for the indication. One of skill in the art would appreciate that the dose may depend upon the weight, gender, and indication. In some embodiments, the composition or formulation is administered as a dose of about 500-4000 mg of the combined herbal extracts per day. In non-limiting embodiments, the composition or formulation is administered as a daily dose of about 500-3500 mg, 500-3000 mg, 500-2500, 500-2000, 500-1500, 500-1000, 1000-4000 mg, 1000-3500 mg, 1000-3000 mg, 1000-2500, 1000-2000, 1000-1500, 1500-4000 mg, 1500-3500 mg, 1500-3000 mg, 1500-2500, 1500-2000, 2000-4000 mg, 2000-3500 mg, 2000-3000 mg, 2000-2500, 2500-4000 mg, 2500-3500 mg, 2500-3000 mg, 3000-4000 mg, 3000-3500 mg, or 3500-4000 mg. In other embodiments, the composition or formulation is administered as a daily dose of 0.1-10 mg/kg of total herbal extract.

An extract of an herb or herbal mixture may be prepared by any conventional methods including, but not limited to, maceration, percolation, infusion, and heat extraction using one or more suitable solvents. In embodiments, the composition may be formed by combining the herb or herbal mixture with one or more solvents for a time and under conditions suitable for preparing the extract. After the herb or herbal mixture and solvent have been in contact for a period of time suitable to form the extract, the solvent and herb(s) are separated by a suitable method, such as filtering or centrifugation. The extract can then be further processed, such as by reducing or dehydrating the extract and/or combining the extract with further ingredients.

Any suitable solvent as known in the art may be used for extraction. Suitable solvents for the extraction process (extraction solvents) include aqueous solvents, water, and aqueous solutions of ethanol. In an embodiment, heat is applied to the solvent/herb mixture. In certain embodiments, the solvent and herbal mixture is heated to boiling for a suitable period of time. In particular embodiments, the solvent/herb mixture is heated for a period exceeding about 1 minute. In further embodiments, the mixture is heated for at least about 1-15 minutes. In other embodiments, the mixture is heated for at least about 1-10, 1-5, 1-4, 1-3, 5-15, 5-10, or 10-15 minutes. In particular, but not limiting, embodiments, the mixture is heated for at least about 1, 2, 3, 4, 5, 10, or 15 minutes. It will be appreciated where each herb is extracted separately, the same or different solvents may be used for each extraction process.

IV. METHODS OF USE

A. Perimenopause, Menopause, and Postmenopause

The methods, kits, and related formulations described herein are used for treating, preventing, or ameliorating the symptoms of perimenopause, menopause, and/or postmenopause for a human subject. The discussion below is with reference to menopause, but will apply equally to perimenopause and/or postmenopause symptoms. Menopause is the 12 months following a woman's last menstrual period. Menopause is associated with vaginal dryness, hot flashes, night sweats (especially due to vasomotor instability), sleep disorders, mood changes, fatigue, weight gain and/or slowed metabolism, among others. Hormone replacement therapy (HT) by administering estrogens has been the standard treatment for menopausal symptoms for decades. However, recent studies have found that the combination of estrogen and progestin increases a woman's risk for breast cancer, stroke, colorectal cancer, etc. (Rossouw et al., *JAMA*, 2002, 288(3):321-333).

In embodiments, the compositions described herein are useful for treating, preventing or ameliorating vasomotor symptoms of menopause including hot flashes, hot flushes, and night sweats. In one particular, but not limiting, embodiment, the compositions are useful for treating hot flashes. Hot flashes are manifested as an increase in skin temperature, and are often accompanied by a sudden onset of sweating on the face, neck and/or chest. Hot flashes may significantly affect the quality of life. Hot flashes may be particularly bothersome at night as they can disturb sleep, leading to fatigue.

The compositions used in the present methods are a combination of 10 botanical agents used in traditional Chinese medicine (TCM) to treat yin deficiency heat.

Figure 2:
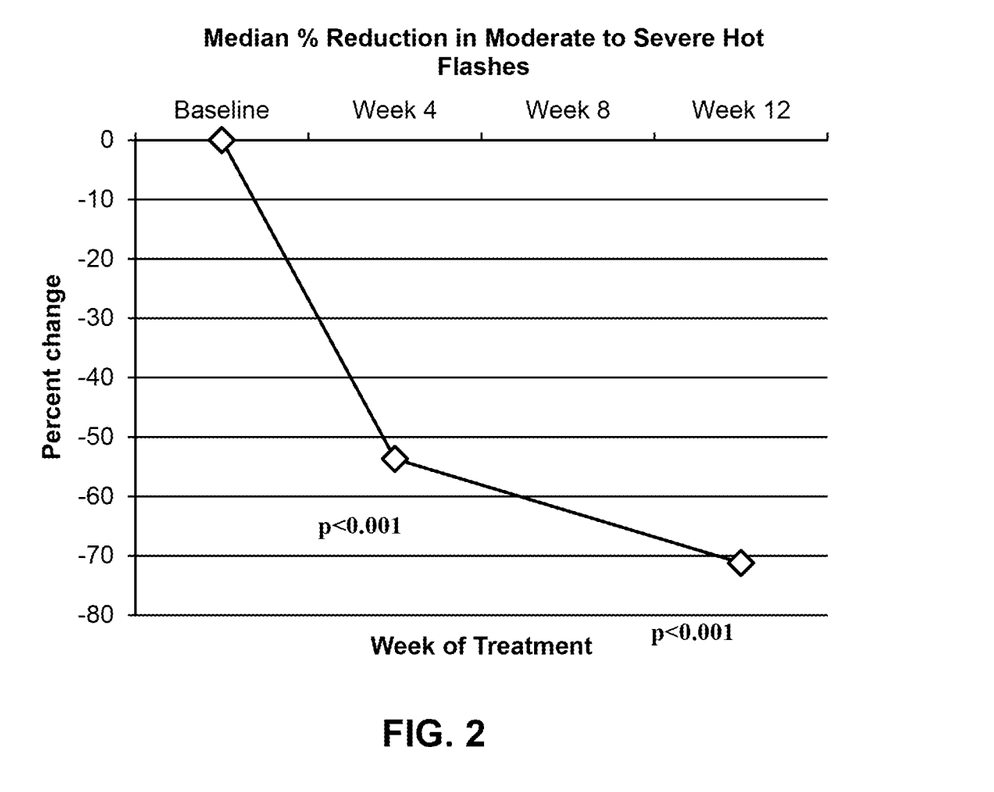
FIG. 2 is a line graph showing the reduction in moderate to severe hot flashes after administration of the composition. The graph shows the median percent change in moderate to severe hot flashes over 12 weeks of treatment from a baseline.
Figure 3:
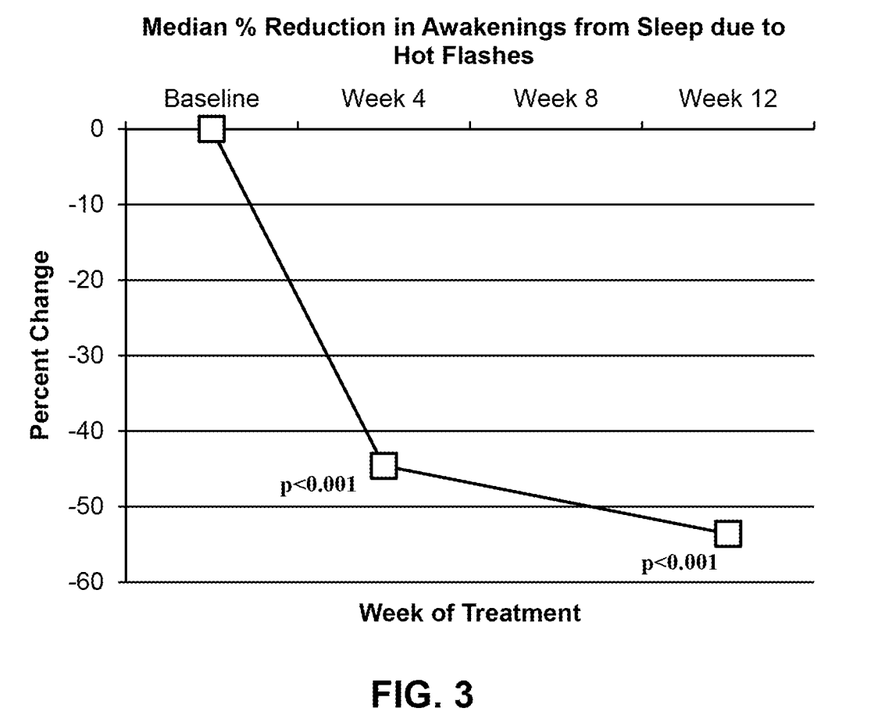
FIG. 3 is a line graph showing the reduction in awakenings from sleep due to hot flashes after administration of the composition. The graph shows the median percent change in awakenings from sleep over 12 weeks of treatment from a baseline.

As described in Example 1, postmenopausal women treated with a composition as described herein for 12 weeks experienced a decline in the frequency and severity of moderate to severe hot flashes. There were statistically significant reductions in the frequency of moderate to severe hot flashes from baseline to weeks 4 and 12 as well as the number of awakenings from sleep due to hot flashes from baseline to week 12. After 4 and 12 weeks of treatment with the formulation of Table 2, the median percent decrease in the frequency of moderate to severe hot flashes was 53.7% ($p<0.001$) and 71.2% ($p<0.001$), respectively. The median percent reduction in awakenings from sleep due to hot flashes from baseline to week 12 was 53.6% ($p<0.001$). Observed median percent changes are presented in FIGS. 2 and 3. The median percent reduction in moderate to severe hot flashes from baseline to 4 weeks was 53.7% ($p<0.001$) and from baseline to 12 weeks was 71.2% ($p<0.001$). The median percent reduction in nighttime awakenings from baseline to week 12 was 53.6% ($p<0.001$).

The present compositions are a selective estrogen receptor beta (ERβ) agonist that does not exhibit binding affinity for estrogen receptor alpha (ERα). As thermoregulatory control centers of the brain are rich with ERβ receptors, selective ERβ agonists may ameliorate hot flashes resulting from fluctuations in stimulation of these receptors. Moreover, stimulation of ERβ receptors is not associated with the in vitro and in vivo breast and uterine cell proliferation inherent in ERα stimulation. Thus, ERβ receptor agonists theoretically do not carry the risk for breast and uterine cancer tumor formation inherent in the use of traditional ERα-based estrogenic treatments.

As described in Example 3, a composition prepared as described in Table 2 was shown to selectively activate transcription through ERβ. A single copy of the vitellogenin A2 ERE upstream of the minimal tk promoter (ERE tk-Luc) was cotransfected into U2OS cells with an expression vector for human ERα or ERβ. After transfection, the cells were treated with increasing amounts of formulation (10, 25, 50, or 100 μg/mL) and luciferase activity was measured. The cells were treated with 10 nM E2 or 10-100 μg/ml of the formulation for 18 h and luciferase activity was measured with the results shown in FIGS. 2A-2B. Unlike estradiol, the formulation did not activate ERE tk-Luc in U2OS cells transfected with ERα (see FIG. 2A). However, the formulation demonstrated activation of ERE tk-Luc in U2OS cells transfected with ERβ (see FIG. 2B). The levels of activation were the same as for E2 for treatment of 50 and 100 μg/mL. Administration of 25 μg/mL of the formulation was nearly the same as administration of E2. Further, administration of 10 μg/mL activated ERE tk-Luc significantly greater than the control.

As described below, there were no significant adverse events after 12 weeks of use. Thus, the compositions described herein are well-tolerated, safe and effective selective ERβ agonist extracts for the treatment of postmenopausal hot flashes.

B. Reducing Cholesterol Levels

In other embodiments, the compositions described herein are useful for treating, preventing or ameliorating conditions associated with high cholesterol levels, hypercholesterolemia. In embodiments, the compositions are useful for lowering total cholesterol and/or lowering low density lipoprotein (LDL) levels. Elevated cholesterol is a major risk factor for coronary heart disease, heart attack and stroke. High total cholesterol is considered 240 mg/dL or above, borderline high cholesterol is considered 200-239 mg/dL of blood, and normal cholesterol levels are less than 180-200 mg/dL. The total cholesterol measures the high density lipoproteins (HDL), LDL and a portion of the triglycerides. Recommended ideal levels of LDL vary based on the subject's risk for heart disease. For subjects at a very high risk of heart disease, ideal LDL levels are below 70 mg/dL. For subjects at risk for heart disease, ideal LDL levels are below 100 mg/dL. LDL levels of 100-129 mg/dL are considered near ideal and 130-159 mg/dL are considered borderline high. LDL levels of 160-189 mg/dL are considered high, and above 190 mg/DL is considered very high.

As shown in Example 2, treatment with the formulation for twelve weeks reduced both the total cholesterol and the LDL levels significantly from the baseline measurements. The mean total cholesterol was reduced from 228.0 to 215.9 mg/dL. Thus, the formulation was effective to reduce the mean total cholesterol level over 5% from the baseline. The mean LDL level was also reduced from 136.4 to 125.9 mg/dL. Thus, the formulation was effective to reduce the mean LDL level over 7% from the baseline.

C. Weight Loss

In another embodiment, the compositions described herein are useful for treating, preventing or ameliorating conditions associated with obesity. In embodiments, the compositions are useful for lowering or reducing weight and/or lowering a subject's body mass index (BMI). As shown in Example 2, treatment with the formulation for twelve weeks reduced both the participant's weight and BMI from the baseline measurements. The participants' mean weight was reduced from 73.2 to 72.3. The mean BMI for the participants was also reduced from 27.2 to 26.8. Thus, the formulation was effective to reduce both the mean participant weight and the participant BMI.

As shown in Example 2, the formulations and compositions described herein are safe for extended use. There were no serious adverse events, no vaginal bleeding, no cases of endometrial hyperplasia or cancer and no significant changes in the double wall endometrial thickness on transvaginal ultrasound after twelve weeks of use.

The formulations and compositions as described herein may be used for an extended period. For treatment of menopausal symptoms, it will be appreciated that the formulation or composition may be administered for as long as the subject is experiencing symptoms. In an embodiment, the formulation or composition is administered for 2 weeks to five years or more. In particular embodiments, the formulation is administered for 2 weeks to 24 months, 2 weeks to 18 months, 2 weeks to 12 months, 2 weeks to 9 months, 2 weeks to 6 months, 2 weeks to 3 months, 2 weeks to 2 months, 2 weeks to 1 month, 4 weeks to 24 months, 4 weeks to 18 months, 4 weeks to 12 months, 4 weeks to 9 months, 4 weeks to 6 months, 4 weeks to 3 months, 4 weeks to 2 months, 6 weeks to 24 months, 6 weeks to 18 months, 6 weeks to 12 months, 6 weeks to 9 months, 6 weeks to 6 months, 6 weeks to 3 months, 6 weeks to 2 months, 8 weeks to 18 months, 8 weeks to 12 months, 8 weeks to 9 months, 8 weeks to 6 months, 8 weeks to 3 months, 8 weeks to 2 months. In some embodiments, the composition or formulation is administered for a period of about 4-24 weeks or about 4-52 weeks.

The composition may be administered by any suitable method including oral or parenteral. It will be appreciated that the composition may be used in conjunction with other therapies.

V. EXAMPLES

The following examples are illustrative in nature and are in no way intended to be limiting. Efforts have been made to ensure accuracy with respect to numbers (e.g., amounts, temperature, etc.) but some errors and deviations should be accounted for. Unless indicated otherwise, parts are parts by weight and temperature is in ° C.

A. Abbreviations

LDL low density lipoproteins
HDL high density lipoproteins
ERα estrogen receptor alpha
ERβ estrogen receptor beta
Estradiol E2
RLU relative light units Example 1

Efficacy Evaluation

A total of 30 postmenopausal women were enrolled to the study and 27 participants completed 12 weeks of treatment with a formulation as in Table 2:

TABLE 2

| Formulation | | |
|---|---|---|
| Herbal Extract | Percent in Capsule | Weight (mg) per capsule |
| Radix Rehmanniae | 12 | 60 |
| Fructus Corni Officinalis | 12 | 60 |
| Radix Dioscoreae Oppositae | 12 | 60 |
| Sclerotium Poriae Cocos | 10 | 50 |
| Cortex Moutan Radicis | 10 | 50 |
| Rhizoma Alismatis Orientalis | 10 | 50 |
| Anemarrhena Rhizome | 10 | 50 |
| Glycyrrhiza uralensis | 10 | 30 |
| Radix Astragali | 6 | 30 |
| Atractylodis Macrocephalae Rhizoma | 8 | 40 |

The formulation was prepared by obtaining a purified aqueous extract of the herbs. A spray-dried power was prepared and formed into capsules. Participants were generally healthy postmenopausal women 40 to 65 years old who reported at least 5 moderate to severe hot flashes per day or 35 per week. The majority of the participants were Caucasian (73.3%). The women were aged 40-65 and the mean age at baseline was 52.7. At baseline, the average frequency of moderate to severe hot flashes was 9.0 per day and the average frequency of awakenings from sleep due to hot flashes was 3.2 per night. All participants experienced a minimum of 5 moderate to severe hot flashes per day. Baseline demographic and clinical characteristics are described in Table 3.

TABLE 3

| Baseline and Demographic Characteristics, Safety Population | |
|---|---|
| Characteristic | Formulation 4 g/day (N = 30) |
| Age | |
| Mean (SD) | 56.6 (4.9) |
| Race | |
| White | 22 (73.3%) |
| Black/African American | 8 (26.7%) |
| Asian | 0 |
| American Indian or Alaska Native | 0 |
| Native Hawaiian or Other Pacific Islander | 0 |
| Refused to answer | 0 |

TABLE 3-continued

Baseline and Demographic Characteristics, Safety Population

| Characteristic | Formulation 4 g/day (N = 30) |
|---|---|
| Ethnicity | |
| Hispanic or Latino | 5 (16.7%) |
| Not Hispanic or Latino | 25 (83.3%) |
| Refused to answer | 0 |
| Body Mass Index (kg/m$^2$) | |
| Mean (SD) | 27.2 (4.5) |
| Length of Time Experiencing Hot Flashes (years) | |
| Mean (SD) | 8.0 (4.7) |
| Time Since Menopause, % | |
| Less than 24 months | 4 (13.3%) |
| 24 months or more | 26 (86.7%) |
| Screening Endometrial Thickness on TVUS (mm) | |
| n | 21 |
| Mean (SD) | 2.03 (1.0) |
| Prior Estrogen User, % | 3 (10.0%) |
| Both Ovaries Removed with or without hysterectomy, % | 7 (23.3%) |
| Hysterectomy and FSH >40 mIU/ml, % | 9 (30.0%) |

To establish a baseline, all participants had a physical examination, including blood pressure and heart rate, a breast and pelvic exam, laboratory tests and, in women with an intact uterus, a transvaginal ultrasound to measure endometrial double wall thickness was completed.

The formulation was administered as 4 500 mg capsules orally, twice a day, about 30 minutes after meals. The study treatment was 4 g/day (total herbs) for 12 weeks.

Hot flash frequency and severity were recorded on a paper diary model. The 7-day diary was completed prior to randomization and during weeks 4, 8 and 12 on study medication. For each hot flash, severity was rated as 1 (mild), 2 (moderate) or 3 (severe). In addition, participants noted on the diary if the hot flash awoke them from sleep. Hot flash diaries were reviewed and collected by the study coordinator at the week 5 visit and at week 12 (study termination). The primary efficacy outcome was median percent change in moderate to severe hot flashes from baseline to 12 weeks of treatment. Secondary endpoints included the median percent change in frequency of moderate to severe hot flashes from baseline to 4 weeks of treatment and median percent change in the frequency of hot flashes that awoke participants from sleep from baseline to 12 weeks of treatment.

There were statistically significant reductions in the frequency of moderate to severe hot flashes from baseline to weeks 4 and 12 as well as the number of awakenings from sleep due to hot flashes from baseline to week 12. After 4 and 12 weeks of treatment with the formulation, the median percent decrease in the frequency of moderate to severe hot flashes was 53.7% (p<0.001) and 71.2% (p<0.001), respectively. The median percent reduction in awakenings from sleep due to hot flashes from baseline to week 12 was 53.6% (p<0.001). Observed median percent changes are presented in FIGS. 2 and 3.

Example 2

Safety Evaluation

To evaluate safety, individual treatment emergent adverse events (TEAEs) events were captured at weeks 2, 5, 8, 12 and 14. Participants were also advised to contact the clinical site by phone or schedule an in-person clinic visit at any time during the trial to report an adverse event. Physical examinations with vital signs were completed at baseline and week 12. All laboratory tests completed at baseline and at study termination, including complete blood counts, chemistry panels and urinalyses were processed by Enzo Central Laboratories. Endometrial safety was assessed by comparing baseline transvaginal ultrasound (TVUS) results for double wall endometrial thickness to the TVUS results at study termination. Diagnostic endometrial biopsies were performed during the study if a participant reported vaginal spotting, vaginal bleeding or if the final endometrial double wall thickness measured by TVUS was over 8 mm. Treatment emergent adverse events were classified using the Medical Dictionary for Regulatory Activities (MedDRA) system.

The safety population included all 30 postmenopausal women enrolled to the study. During the study, there were no serious adverse events, no cases of abnormal vaginal bleeding, no laboratory abnormalities and no cases of endometrial double wall thickness >8 mm on transvaginal ultrasound while on treatment or at study termination. Three participants (10%) discontinued study treatment due to rash, stomach pains and influenza. The first 2 AEs were coded as related to study treatment. A fourth participant reported abdominal bloating which was coded as related to study treatment and a fifth participant reported experiencing bloody exudate from her nipple. The nipple discharge could not be repeated during a follow up visit with a surgeon and a repeat mammogram showed no changes from baseline or any evidence of suspicious lesions.

Of the 30 participants in the study, 21 or 70% (had a uterus. All women with an intact uterus had a transvaginal ultrasound at baseline and all had this test repeated at the end of the trial. Mean endometrial thickness was 2.03 mm at baseline and 2.38 at 12 weeks; there were no differences mean endometrial thickness (p=0.16).

TABLE 4

Number (%) of participants reporting treatment emergent adverse events

| MedDRA SOC | Adverse Event | Formulation 4 g/day N (%) |
|---|---|---|
| Gastrointestinal Disorders | Abdominal distension/bloating | 1 (3.3%) |
| | Gastrointestinal pain | 1 (3.3%) |
| Infections and Infestations | Influenza | 1 (3.3%) |
| Skin and Subcutaneous Disorders | Rash | 1 (3.3%) |

Treatment adherence was measured by diaries at the week 5 and week 12/early termination visits. Table 4 is a summary of adherence with study medication by patient reported diaries. The mean treatment compliance was 91.1% (range 83%-100%).

There was a statistically significant decrease in BMI, total cholesterol and LDL cholesterol.

TABLE 5

Weight, BMI, Blood Pressure and Cholesterol

| | Baseline | | | End of Study | | P-value |
|---|---|---|---|---|---|---|
| | Mean | SD | N | Mean | D | (Paired t-test) |
| Weight | 0 73.2 | 11.9 | 29 | 72.3 | 1.9 | 0.0570 |
| BMI | 0 27.2 | 4.5 | 29 | 26.8 | .5 | 0.0324 |
| Diastolic Blood Pressure | 0 79.6 | 6.3 | 29 | 79.3 | .8 | 0.6766 |
| Systolic Blood Pressure | 0 118.9 | 10.0 | 29 | 111.6 | .5 | 0.2163 |
| Total Cholesterol | 0 228.0 | 40.8 | 29 | 215.9 | 9.6 | 0.0098 |
| Triglycerides | 0 124.5 | 78.6 | 29 | 140.0 | 19.8 | 0.2563 |
| HDL | 0 66.3 | 19.1 | 29 | 63.7 | 8.8 | 0.2102 |
| LDL | 0 136.4 | 35.1 | 29 | 125.9 | 3.5 | 0.0090 |

Example 3

Estrogen Receptor Selectivity

Figure 1A:
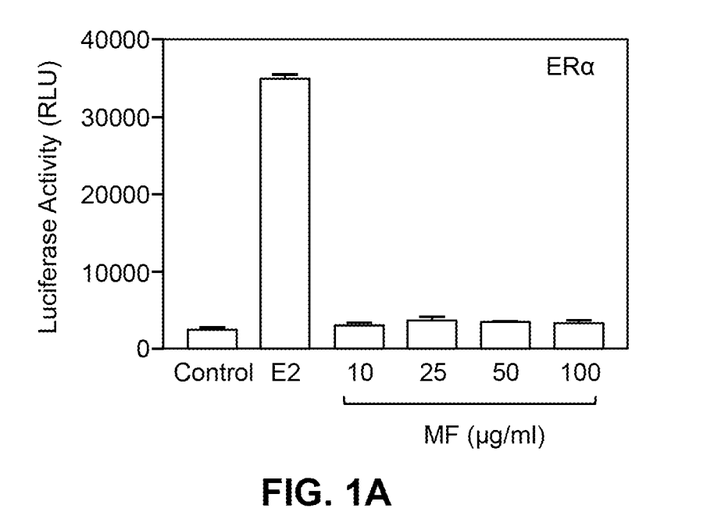
FIGS. 1A-1B are bar graphs comparing the activity of the composition to estradiol ($E_2$) and a control on ERα and ERβ expressing cells.
Figure 1B:
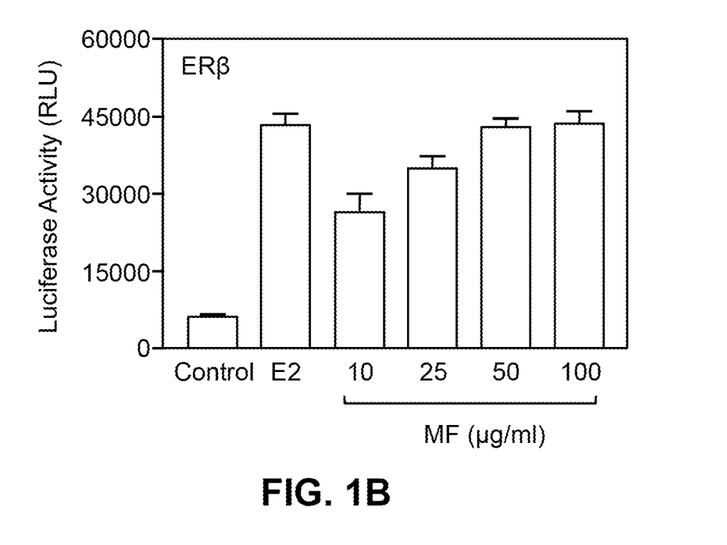

It is well established that the effects of estrogens on hot flashes are mediated by estrogen receptors. ERα and ERβ are both present in the brain. To determine if the present compositions can regulate ERα and/or ERβ, human U2OS osteosarcoma cells were co-transfected with a classical estrogen response element (ERE) upstream of a minimal thymidine kinase (tk) promoter (ERE-tk-Luc) and expression vectors for human ERα and ERβ. An herbal extract composition as in Table 2 produced a dose-dependent activation of ERE-tk-Luc with ERβ (FIG. 1B), whereas no significant activation was observed with ERα (FIG. 1A). These results demonstrate that the present compositions are ERβ-selective agonists.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not necessarily to the text of this application, in particular the claims of this application, in which instance, the definitions provided herein are meant to supersede.

What is claimed is:

1. A method of treating hot flashes associated with peri-menopause, menopause, or post-menopause, comprising:
    administering a therapeutically effective amount of a composition consisting essentially of herbal extracts of 5-20 wt % Radix Rehmanniae , 5-20 wt % Fructus Corni Officinalis, 5-20 wt % Radix Dioscoreae Oppositae, 5-15 wt % Sclerotium Poriae Cocos, 5-15 wt % Cortex Moutan Radicis, 5-15 wt % Rhizoma *Alismatis Orientalis,* 5-15 wt % Anemarrhena Rhizome, 5-15 wt % *Glycyrrhiza uralensis,* 2-10 wt % Radix Astragali, and 5-15 wt % Atractylodis Macrocephalae Rhizoma.

2. The method of claim 1, wherein said administering reduces at least one of the frequency, the duration, the severity, the number of nighttime awakenings, or the number of hot flashes per day.

3. The method of claim 1, wherein the composition is administered as a dose of 500-4000 mg of the combined herbal extracts per day.

4. The method of claim 1, wherein about 0.1-10 mg/kg of the composition is administered daily.

5. The method of claim 1, wherein the composition is administered for a period of about 4-52 weeks.

6. The method of claim 1, wherein the composition is administered about 30 minutes after a meal.

7. The method of claim 1, wherein administration of the composition selectively activates ERβ.

\* \* \* \* \*